US009371561B2

(12) United States Patent
Afzali-Ardakani et al.

(10) Patent No.: US 9,371,561 B2
(45) Date of Patent: Jun. 21, 2016

(54) DNA SEQUENCING USING A SUSPENDED CARBON NANOTUBE

(71) Applicant: GLOBALFOUNDRIES INC., Grand Cayman (KY)

(72) Inventors: Ali Afzali-Ardakani, Ossining, NY (US); Aaron D. Franklin, Croton on Hudson, NY (US); George S. Tulevski, White Plains, NY (US)

(73) Assignee: GLOBALFOUNDRIES INC., Grand Cayman (KY)

( * ) Notice: Subject to any disclaimer, the term of this patent is extended or adjusted under 35 U.S.C. 154(b) by 411 days.

(21) Appl. No.: 14/014,791

(22) Filed: Aug. 30, 2013

(65) Prior Publication Data

US 2015/0060275 A1    Mar. 5, 2015

(51) Int. Cl.
*C12Q 1/68* (2006.01)
*G01N 27/447* (2006.01)
*G01N 33/487* (2006.01)

(52) U.S. Cl.
CPC ........ *C12Q 1/6869* (2013.01); *G01N 27/44791* (2013.01); *G01N 33/48721* (2013.01)

(58) Field of Classification Search
CPC ... G01N 27/447; G01N 27/02; G01N 33/487; H01L 21/44; B82Y 30/00; B82Y 15/00; C12Q 1/686
See application file for complete search history.

(56) References Cited

U.S. PATENT DOCUMENTS

| | | |
|---|---|---|
| 7,005,264 B2 | 2/2006 | Su et al. |
| 7,709,298 B2 | 5/2010 | Li |
| 8,092,697 B2 | 1/2012 | Branton et al. |
| 2005/0065741 A1* | 3/2005 | Segal ............... G01N 27/4146 702/57 |
| 2008/0135892 A1 | 6/2008 | Finnie |
| 2008/0233744 A1* | 9/2008 | Kaul ..................... B82Y 10/00 438/684 |
| 2011/0177493 A1 | 7/2011 | Lu |
| 2012/0326126 A1* | 12/2012 | Chen ................ H01L 29/42384 257/29 |

OTHER PUBLICATIONS

A. D. Franklin et al., "Contacts-First Self-Aligned Carbon Nanotube Transistor with Gate-All-Around," U.S. Appl. No. 13/584,199, filed Aug. 13, 2012; 18 pages.

N. R. Franklin et al., "Integration of suspended carbon nanotube arrays into electronic devices and electromechanical systems," Applied Physics Letters, vol. 81.No. 5, 2002, pp. 913-915.

(Continued)

*Primary Examiner* — Jennifer Dieterle

(74) *Attorney, Agent, or Firm* — Thompson Hine LLP

(57) ABSTRACT

A technique is provided for forming a nanodevice for sequencing. A bottom metal contact is disposed at a location in an insulator that is on a substrate. A nonconducting material is disposed on top of the bottom metal contact and the insulator. A carbon nanotube is disposed on top of the nonconducting material. Top metal contacts are disposed on top of the carbon nanotube at the location of the bottom metal contact, where the top metal contacts are formed at opposing ends of the carbon nanotube at the location. The carbon nanotube is suspended over the bottom metal contact at the location, by etching away the nonconducting material under the carbon nanotube to expose the bottom metal contact as a bottom of a trench, while leaving the nonconducting material immediately under the top metal contacts as walls of the trench.

13 Claims, 11 Drawing Sheets

(56) References Cited

OTHER PUBLICATIONS

J. J. Kasianowicz et al., "Characterization of Individual Polynucleotide Molecules Using a Membrane Channel," Proc. Natl. Acad. Sci. USA, vol. 93, 1996, pp. 13770-13773.

T. Sharf et al., "Fabrication of low-noise carbon nanotube field-effect transistor biosensors," 2011 11th IEEE Conference on Nanotechnology (IEEE-NANO), 2011, pp. 122-125.

T. Sharf et al., "Origins of Charge Noise in Carbon Nanotube Field-Effect Transistor Biosensors," Nano Letters, vol. 12, No. 12, 2012, pp. 6380-6384.

* cited by examiner

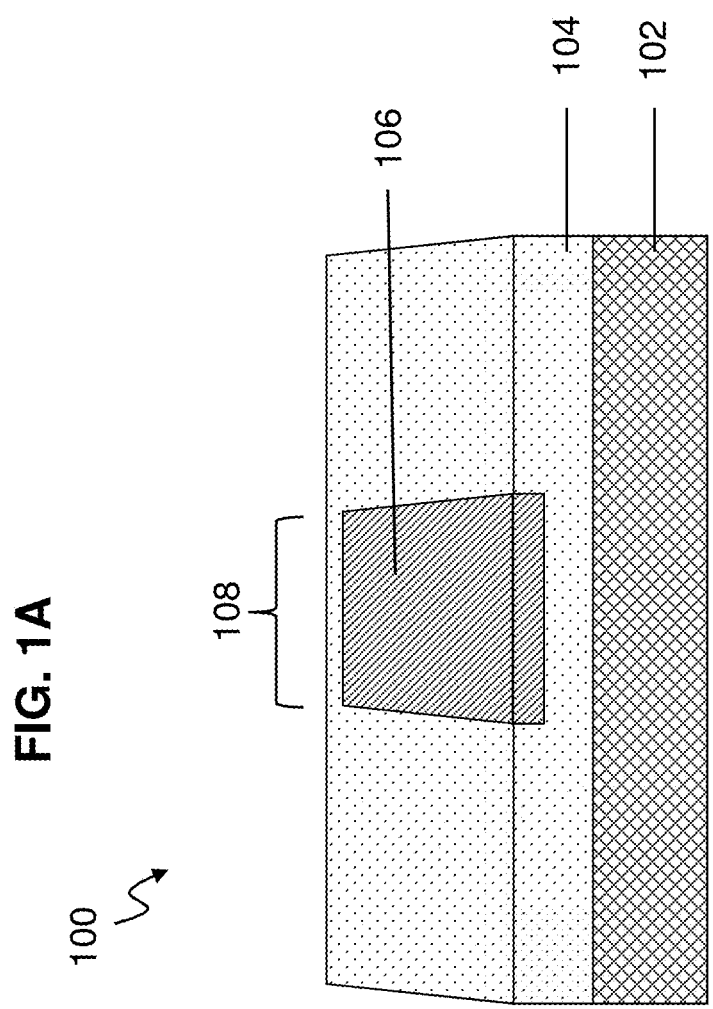

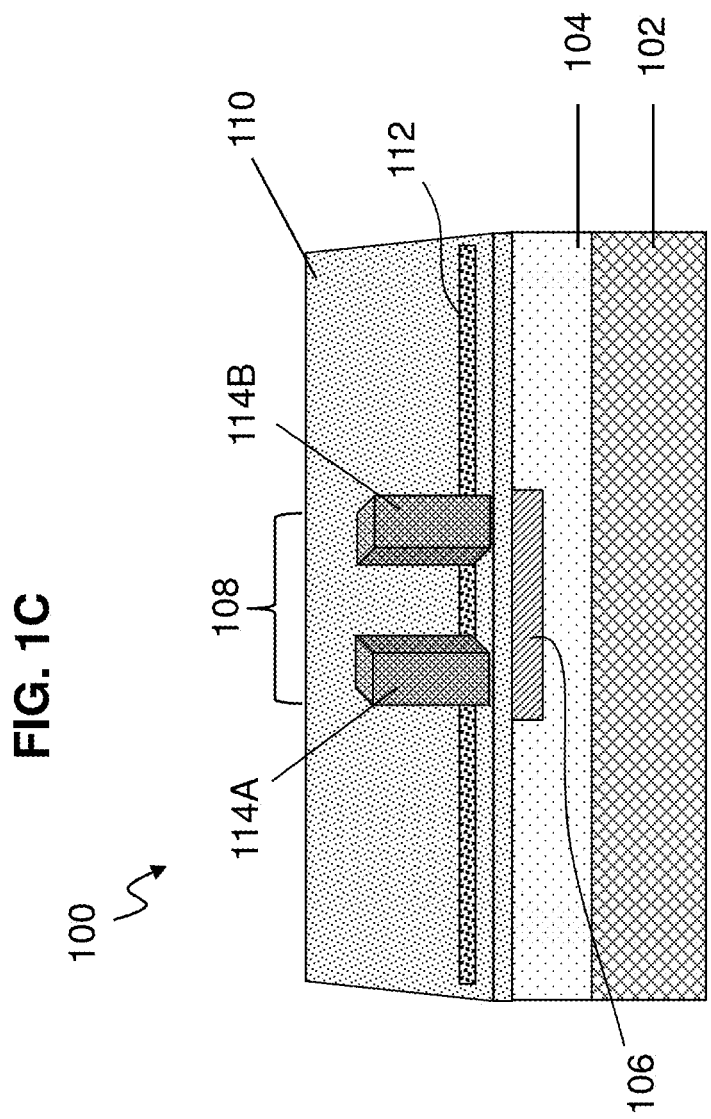

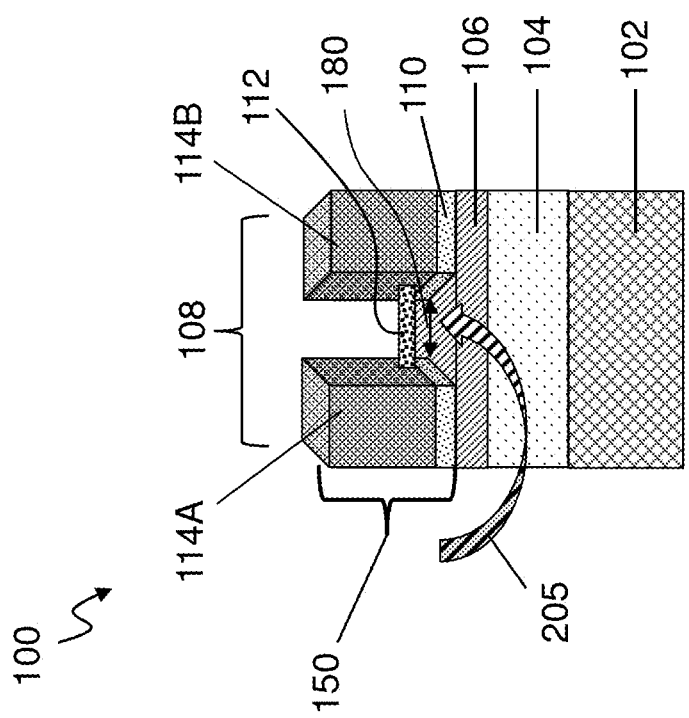

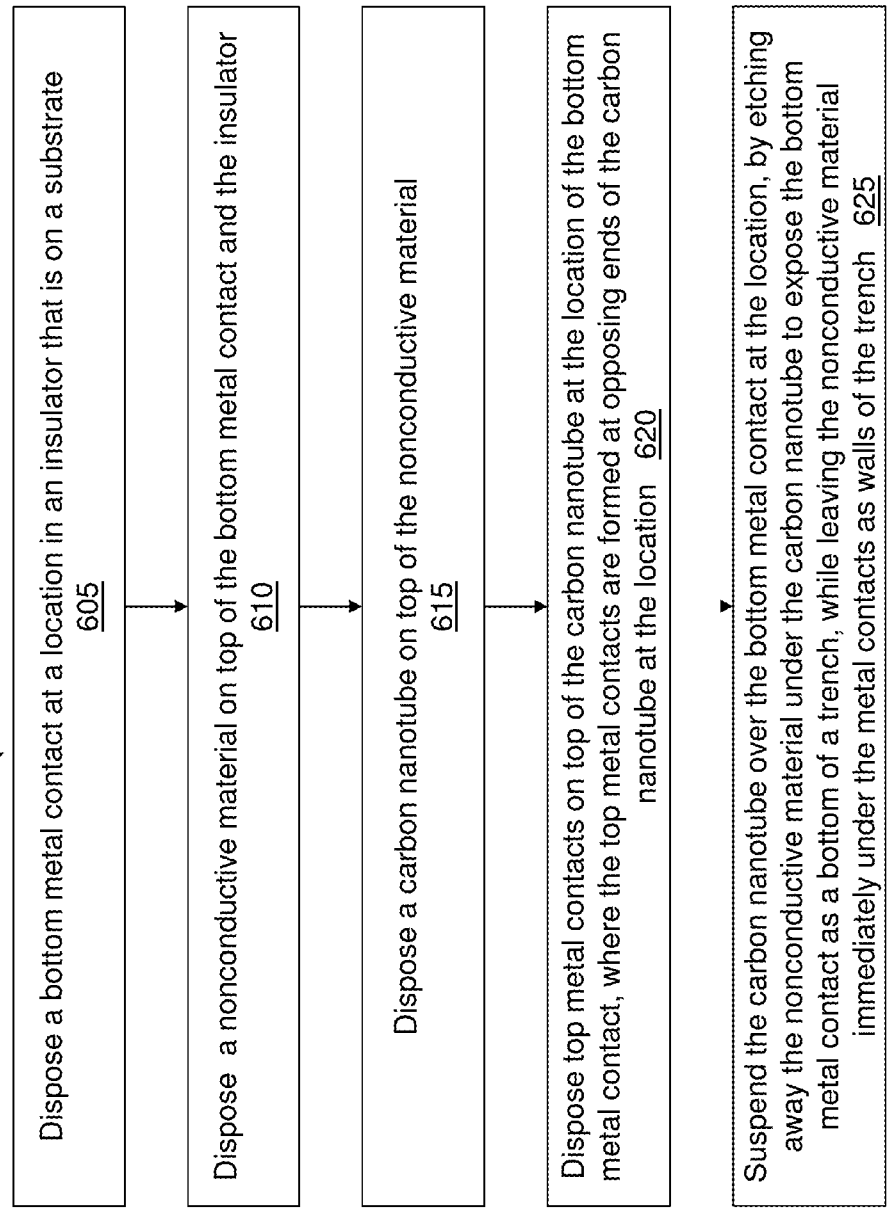

Translocate a target molecule in a trench of a nanodevice, where the nanodevice includes a carbon nanotube suspended over the trench by top metal contacts, and includes a bottom metal contact as a bottom of the trench  705

↓

Measure a first current flowing between the top metal contacts through the carbon nanotube  710

↓

Measure a change in the first current based on a base of the target molecule in the trench interacting with the carbon nanotube to change a conductance of the carbon nanotube  715

DNA SEQUENCING USING A SUSPENDED CARBON NANOTUBE

BACKGROUND

The present invention relates generally to nanodevices, and more specifically, to a nanodevice with one or more suspended carbon nanotubes for sequencing.

Nanopore sequencing is a method for determining the order in which nucleotides occur on a strand of deoxyribonucleic acid (DNA). A nanopore (also referred to as pore, nanochannel, hole, etc.) can be a small hole in the order of several nanometers in internal diameter. The theory behind nanopore sequencing is about what occurs when the nanopore is submerged in a conducting fluid and an electric potential (voltage) is applied across the nanopore. Under these conditions, a slight electric current due to conduction of ions through the nanopore can be measured, and the amount of current is very sensitive to the size and shape of the nanopore. If single bases or strands of DNA pass (or part of the DNA molecule passes) through the nanopore, this can create a change in the magnitude of the current through the nanopore. Other electrical or optical sensors can also be positioned around the nanopore so that DNA bases can be differentiated while the DNA passes through the nanopore.

The DNA can be driven through the nanopore by using various methods, so that the DNA might eventually pass through the nanopore. The scale of the nanopore can have the effect that the DNA may be forced through the hole as a long string, one base at a time, like thread through the eye of a needle. Recently, there has been growing interest in applying nanopores as sensors for rapid analysis of biomolecules such as deoxyribonucleic acid (DNA), ribonucleic acid (RNA), protein, etc. Special emphasis has been given to applications of nanopores for DNA sequencing, as this technology holds the promise to reduce the cost of sequencing below $1000/human genome.

SUMMARY

According to one embodiment, a method of forming a nanodevice for sequencing is provided. The method includes disposing a bottom metal contact at a location in an insulator that is on a substrate, disposing a nonconducting material on top of the bottom metal contact and the insulator, and disposing a carbon nanotube on top of the nonconducting material. The method includes disposing top metal contacts on top of the carbon nanotube at the location of the bottom metal contact, in which the top metal contacts are formed at opposing ends of the carbon nanotube at the location. The method includes suspending the carbon nanotube over the bottom metal contact at the location, by etching away the nonconducting material under the carbon nanotube to expose the bottom metal contact as a bottom of a trench, while leaving the nonconducting material immediately under the top metal contacts as walls of the trench.

According to one embodiment, a method of sequencing is provided. The method includes translocating a target molecule in a trench on a substrate of a nanodevice, where the nanodevice includes a carbon nanotube suspended over the trench by top metal contacts, and includes a bottom metal contact as a bottom of the trench. A buffer solution is passed both below and above the carbon nanotube, where the carbon nanotube is functionalized with an organic compound having two different functional groups on either end in which one functional group attaches to the carbon nanotube and another functional group interacts with the target molecule. The method includes measuring a first current flowing between the top metal contacts through the carbon nanotube, and measuring a change in the first current based on a base of the target molecule in the trench interacting with the carbon nanotube to change a conductance of the carbon nanotube.

According to one embodiment, a device for sequencing is provided. The device includes a bottom metal contact formed at a location in an insulator that is on a substrate, a nonconducting material disposed on top of the bottom metal contact and the insulator, and a carbon nanotube disposed on top of the nonconducting material. The top metal contacts are disposed on top of the carbon nanotube at the location of the bottom metal contact, where the top metal contacts are formed at opposing ends of the carbon nanotube at the location. The carbon nanotube is suspended over the bottom metal contact at the location, based on etching away the nonconducting material under the carbon nanotube to expose the bottom metal contact as a bottom of a trench, while leaving the nonconducting material immediately under the top metal contacts as walls of the trench.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

FIGS. 1A through 1D illustrate perspective views of a method of forming a device with a trench according to an embodiment, in which:

FIG. 1A illustrates an electrically insulating substrate with an embedded bottom metal contact;

FIG. 1B illustrates depositing a nonconducting material and carbon nanotube on the device;

FIG. 1C illustrates depositing two top metal contacts on the device; and

FIG. 1D illustrates suspending the carbon nanotube over the bottom metal contact and the trench.

FIG. 2 illustrates a perspective view of the (final) device with the suspended carbon nanotube according to an embodiment.

FIG. 6 illustrates a method of forming the device for sequencing according to an embodiment.

FIG. 7 illustrates a method of sequencing with the device according to an embodiment.

DETAILED DESCRIPTION

Figure 1B:
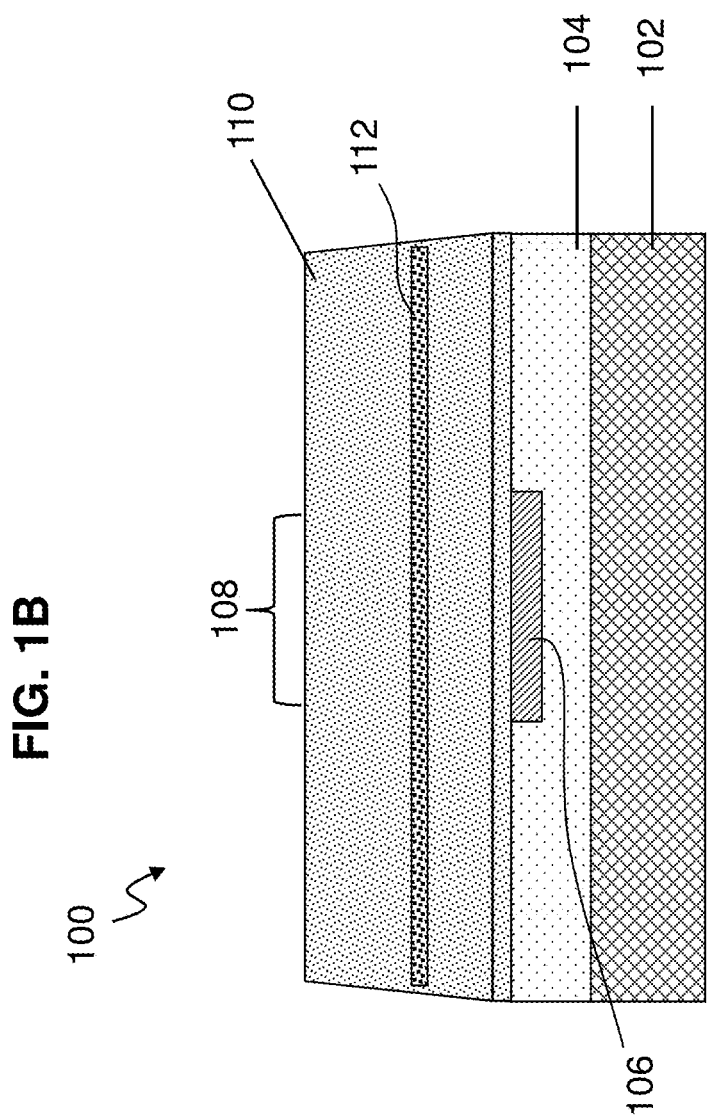

One of the recognized hurdles in the scientific world is to engineer a device that can efficiently and effectively sequence DNA. To sequence DNA means to determine the order of nucleotides in anything from individual genes to entire genomes. While many devices and techniques have been developed over the years, there is still recognition for more rapid throughput and greater precision in sequencing. One approach of intense study is that of nanopore sequencing, where a strand of DNA is immersed in an ionic medium and passed through a nanopore that contains a series of electrodes. When a nucleotide on the DNA obstructs the current between the nanopore electrodes it is detected, providing a unique disruption based upon the type of nucleotide. In the scientific world, the difficulty is in fabricating such nanopores at the needed dimensions in a cost-effective and reproducible manner.

Embodiments offer a solution to this difficulty by providing a structure or nanodevice (as a chip) that is able to sequence the DNA or RNA in a fashion similar to that of the nanopore sequencing using trenches in a substrate rather than small pores.

Embodiments include a device that can sequence DNA using a carbon nanotube (CNT) that is suspended over a narrow trench. In this technique, the idea is that a single CNT is contacted by (top) metal electrodes on either side of a trench and at the bottom of the trench is a second electrode. Immersing the chip in an ionic solution creates a current between the CNT and the bottom electrode. DNA passes through the trench, with each nucleotide of the strand disrupting the current between the bottom electrode and the CNT in a unique way, thus providing the sequence of the DNA. One advantage is that such a trench structure can be readily fabricated using a crystalline silicon substrate and common wet etching and does not require the challenging fabrication of nanopores. In addition to being submersed, an embodiment includes a device that has a reservoir built in that allows one to flow the solution from one reservoir, through the channel, and into another reservoir.

FIGS. 1A through 1D illustrate perspective views of a method of forming nanodevice 100 with a trench according to an embodiment.

FIG. 1A illustrates that the nanodevice 100 has an electrically insulating substrate 102 which may be a silicon wafer, a germanium wafer, and/or a combination of both. An oxide layer 104 may be deposited (e.g., grown) on top of the substrate 102. The oxide layer 104 acts as an insulator, and the oxide layer 104 be any material including silicon dioxide, germanium oxide, etc. As an example, the oxide layer 104 is greater than 100 nanometers (nm) thick (e.g., the oxide layer 104 may be may be 1 micrometer (μm) thick).

A bottom metal contact 106 is deposited on the oxide layer 104 in order to embed the bottom metal contact 106 in the oxide layer 104 at a location 108. The following is one example of embedding the bottom metal contact 106 in the oxide layer 104. A cavity is etched in the oxide layer 104 at location 108. The cavity may be etched using a mask (such as photolithography) and wet etchant, and/or etched using transmission electron microscopy (TEM) (e.g., via an electron microscope). Next, a film of metal (i.e., to form the bottom metal electrode 106) is deposited in the cavity and on top of the oxide layer 104. Chemical mechanical polishing (CMP) is performed (on top of nanodevice 100) to remove the excess metal from the top of the oxide layer 104 and to planarize the bottom metal contact 106 (which smooths its top surface) within the cavity. This results in the bottom metal contact 106 being embedded in the oxide layer 104 as a smooth planar surface (e.g., the top surface of the bottom metal contact 106 is level with the top surface of the oxide layer 104).

FIG. 1B illustrates depositing or transferring a thin layer of nonconducting material 110 directly on top of both the embedded bottom metal contact 106 and the oxide layer 104. In one case, the thin layer of nonconducting material 110 is deposited or transferred to be only a few nanometers (nm) thick, such as 5 to 8 nm thick. In another case, a thicker nonconducting material 110 may be deposited/transferred initially, and then controllably etched down to a sub-10 nm thickness (e.g., 5 to 8 nm thick). The thickness of the nonconducting material 110 determines the depth of the trench (trench 180 discussed below).

Particularly, the deposited/transferred nonconducting material 110 may be silicon with a <110> crystal surface orientation. As discussed below, the <110> crystal surface orientation allows for a wet etchant (e.g., KOH) to be used to provide a cleanly vertical etch (i.e., anisotropic etch) to the thin silicon <110> without undercutting top metal contacts (discussed further below).

In FIG. 1B, a carbon nanotube 112 is placed/transferred on top of the nonconducting material 110 such that the carbon nanotube (CNT) 112 is positioned to horizontally extend across the embedded bottom metal contact 106 at the location 108.

FIG. 1C illustrates that two top metal contact 114A and 114B (generally referred to as top metal contacts 114) are deposited directly on top of both the carbon nanotube 112 and the nonconducting material 110 at the location 108. The top metal contacts 114 are both electrically and physically contact to the carbon nanotube 112. The top metal contacts 114 may be palladium (Pd), gold, silver, etc.

The top metal contact 114A is horizontally separated from (spaced apart) the top metal contact 114B by a distance of, for example, 20-100 nm (nanometer). The two top metal contacts 114 may be formed by standard lithographic processing. In one case, a patterned mask may be applied on top of the carbon nanotube 112 and the nonconducting material 110, and the metal (e.g., 1 to 5 μm thick) is deposited on the patterned mask. The patterned mask (along with the metal on top) is removed to leave the two top metal contacts 114A and 114B according to the pattern. In another case, the metal is deposited on top of the carbon nanotube 112 and the nonconducting material 110, and a patterned mask is deposited to protect the metal underneath, while the exposed metal is removed. When the patterned mask is removed, the two top meal contacts 114A and 114B remain according to the pattern.

Figure 1D:
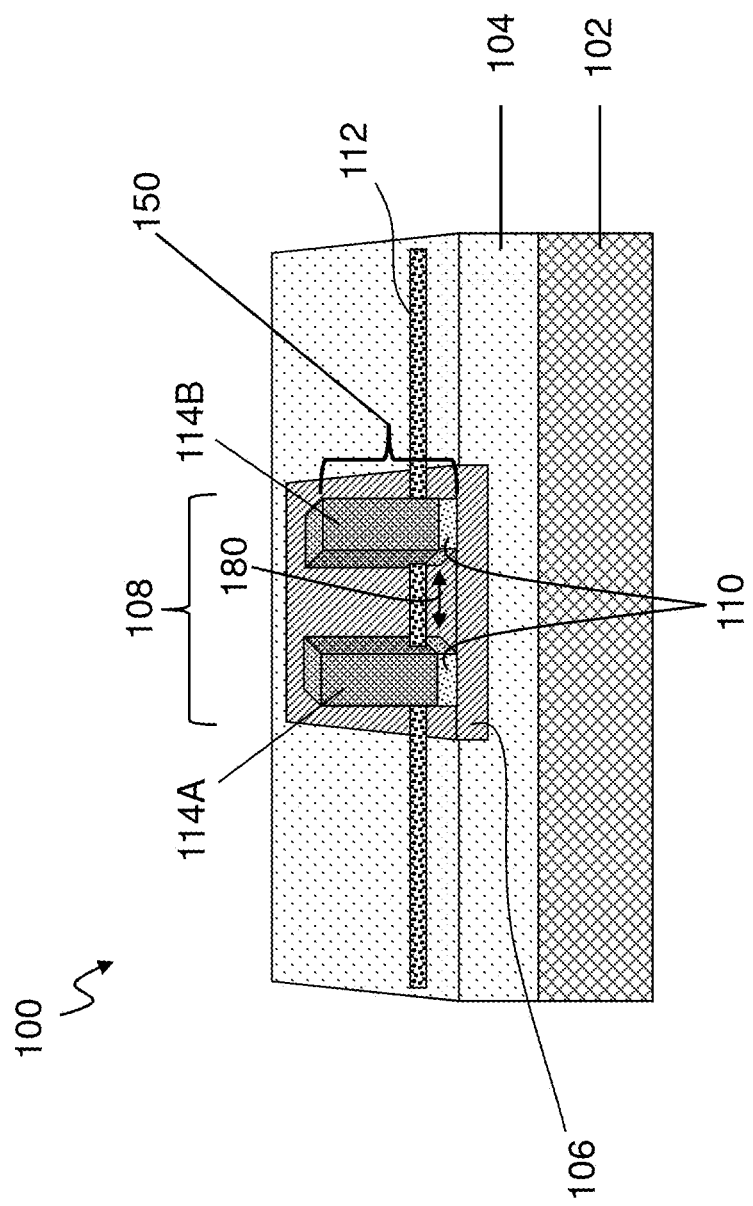

FIG. 1D illustrates suspending the carbon nanotube 112 over the bottom metal contact 106 at the location 108, in which the two top metal contacts 114 each serve as a mask for creating the trench 180. For example, a wet etch, such as potassium hydroxide (KOH) or tetramethylammonium hydroxide (TMAH), may be utilized to anisotropically etch away the nonconducting material 110 (e.g., silicon <110>) except from under the two top metal contacts 114. The nonconducting material 110 underneath the two top metal contacts 114 is masked from the wet etchant. Because of the anisotropic etching of the nonconducting material 110 (e.g., silicon with <110> crystalline surface orientation) to leave the thin layer of nonconducting material 110 underneath the each respective top metal contact 114A and 114B, the anisotropic etching results in two vertical pillars 150 which comprise the top metal contacts 114 and the nonconducting material 110 underneath. Under the now suspended carbon nanotube 112, a trench 180 is formed between the remaining nonconducting material 110 of the vertical pillars 150. As can been seen, the walls of the trench 180 are formed of nonconducting material 110 of the vertical pillars 150 while the bottom of the trench 180 is the exposed bottom metal contact 106. As one example, the height of the walls (i.e., depth) of the trench may be 5 nm.

According to an embodiment, FIG. 2 illustrates a perspective view of the (final) nanodevice 100 with the suspended carbon nanotube 112 (in direct electrical and physical contact with the top metal contacts 114) as one electrode and the embedded bottom metal contact 106. The structure of the nanodevice 100 has the trench 180 that has a length determined by the length of the top metal contacts 114A and 114B. The length of the top metal contacts 114 may be, for example, 100-1000 nm. The distance separating the two top metal contacts 114A and 114B determines the width of the trench 180. The width of the trench may be, for example, 20-100 nm.

In FIG. 2, an arrow 205 shows the trench 180 through which a DNA molecule passes, disrupting the ionic current between the suspended carbon nanotube 112 (above) and the underlying embedded bottom metal contact 112.

Figure 3:
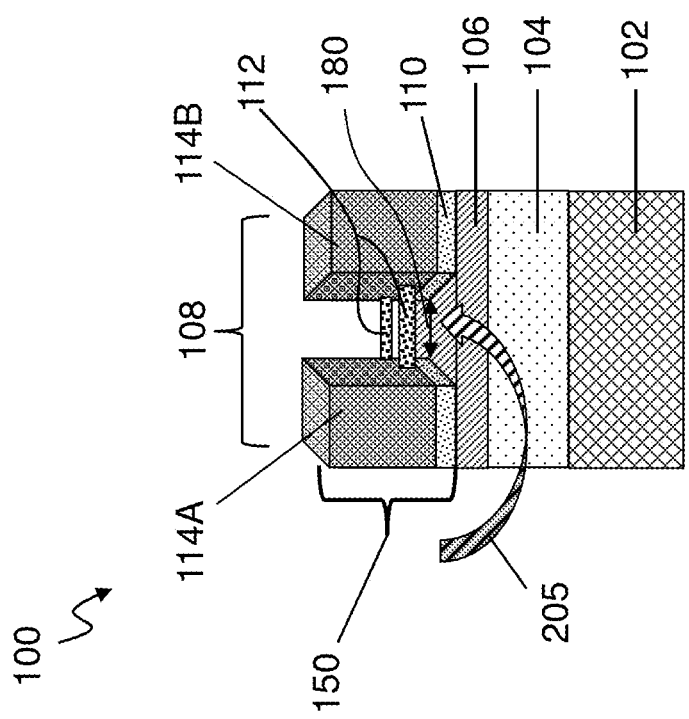
FIG. 3 illustrates a perspective view of the device with multiple carbon nanotubes according to an embodiment.

FIG. 3 illustrates a perspective view of the nanodevice 100 with multiple carbon nanotubes according to an embodiment. Note that multiple bottom metal contacts 106 may be separately embedded (in a column but not touching) and each embedded metal contact 106 has its own carbon nanotube 112 positioned across, as discussed above.

In FIG. 3, the arrow 205 represents that DNA molecule travels underneath both of the carbon nanotubes 112, and the thus the ionic current can be separately measured by the two carbon nanotubes 112.

Figure 4:
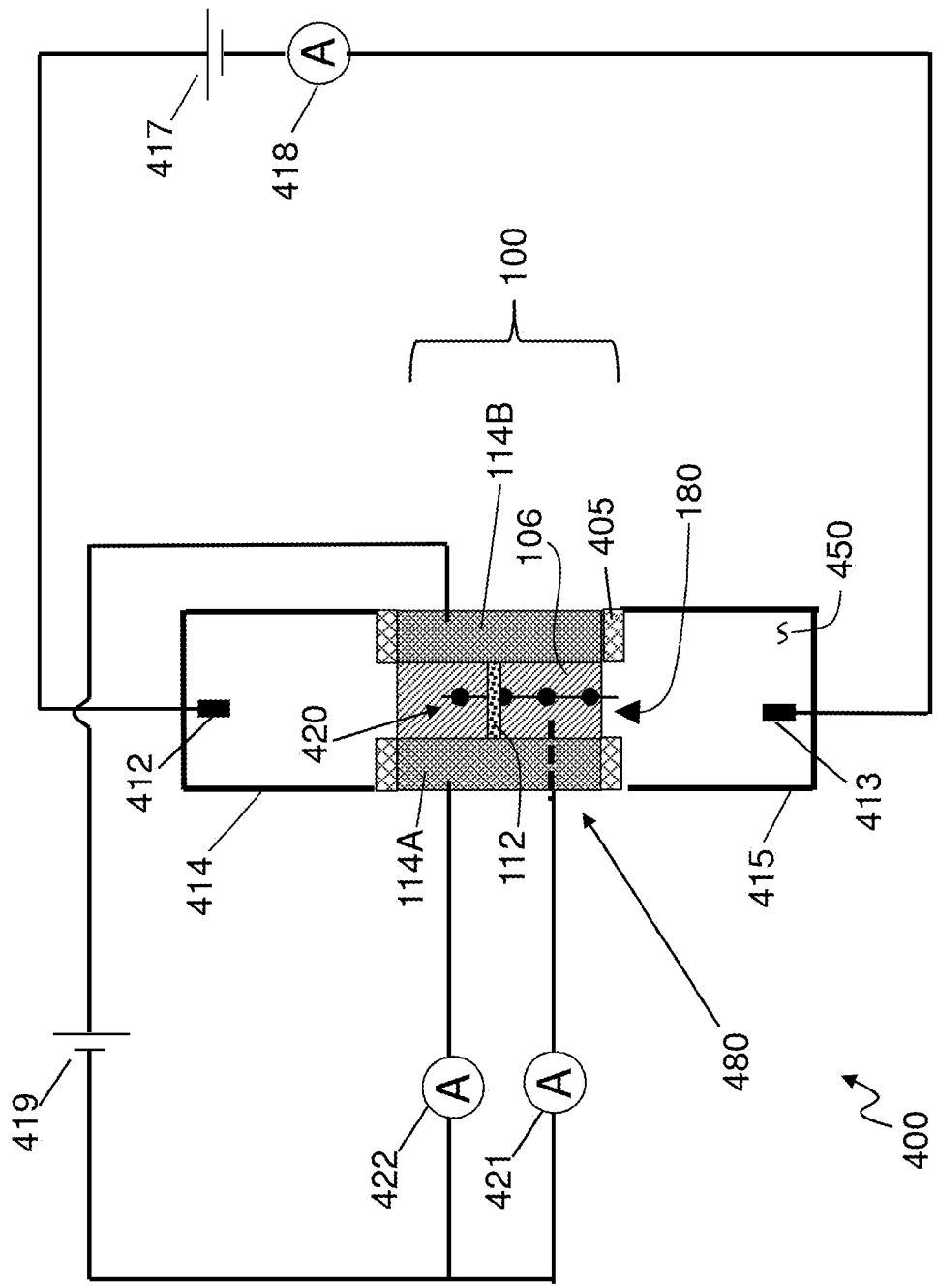
FIG. 4 illustrates a schematic of a system for sequencing using the device according to an embodiment.

FIG. 4 illustrates a schematic of a system 400 for sequencing using the nanodevice 100 according to an embodiment. As discussed above, the nanodevice 100 includes the electrically insulating substrate 102 (wafer), the oxide layer 104, the embedded bottom metal contact 106, the nonconducting material 110 underneath the two top metal contacts 114A and 114B (which form the vertical pillars 150), and the suspended carbon nanotube 112. Dashed lines illustrate a connection 480 underneath (the device 100) to the bottom metal contact 106. The bottom metal contact 106 is connected to the negative polarity of voltage source 419 though an ammeter 421.

In the system 400, two reservoirs 414 and 415 are attached to opposite sides of the trench 180. Each reservoir 414 and 415 is attached and sealed to respective ends of the nanodevice 100, such that buffer solution 450 can flow in the trench 180 and in the reservoirs 414 and 415. Sealing material 405 (which may include O-rings, epoxy, etc.) is utilized to seal the two reservoirs 414 and 415 to opposite ends of the trench 180 (nanodevice 100). One skilled in the art understands how to seal the ends of the nanodevice 100 to respective reservoirs 414 and 415 using standard techniques in the art. The buffer solution 450 may be a salt solution (e.g., such as NaCl) capable of conducting electricity. The buffer solution 450 only flows in the trench 180 and only contacts the bottom metal contact 106 and the side walls of nonconducting material 110 (underneath the top metal contacts 114A and 114B). However, the buffer solution 450 does not contact the top metal contacts 114A nor the carbon nanotube 112, and only contacts the bottom metal contact 106.

Electrode 412 is in one reservoir 414, and electrode 413 is in the other reservoir 415. The electrodes 412 and 413 are connected to a voltage source 417 for driving a target molecule 420 into the trench 180. Electrodes 412 and 413 may be silver/silver chloride, or platinum for example. The reservoirs 415 and 414 are the inlet and outlet, respectively, for the buffer solution 450, and reservoirs 414 and 415 hold the DNA, RNA, and/or protein samples for sequencing.

Note that the carbon nanotube 112 is a functionalized carbon nanotube 112 that has been coated with an organic coating. The organic compound can be covalently attached to the carbon nanotube 112 or non-covalently attached (i.e. via pi-pi interactions). The organic coating can be any organic coating that has/forms a transient bond, such as a hydrogen bond, with individual DNA bases (or RNA bases). By the transient bond, the negatively charged DNA molecule 420 will be trapped inside the trench 180 against thermal agitation/motion of the buffer solution 450. The transient bond means that a single DNA base is attached to the functionalized carbon nanotube 112. With a predefined voltage applied by the voltage source 417, the transient bonds can be broken and the negatively charged DNA molecule can be driven through the trench 180 via the electrical field produced by the voltage source 417. Examples of organic coatings include compounds that can perform hydrogen bond with nucleotides, such as, e.g., carboxylic acids, phosphonic acids, amides and cyclic bases like imidazole or benzimidazoles. These functionalities can be introduced as covalently functionalized moieties via reaction of functionalized diazonium salts or via pi-pi interactions of functionalized condensed aromatic compounds like pyrenebutyric acids.

In the system 400, the target molecule 420 is the molecule being analyzed and/or sequenced. As an example DNA sample, the system 400 may include a single stranded DNA molecule 420 that is passing through the trench 180. The DNA molecule 420 has bases (A, G, C, and T) represented as solid ovals.

The DNA molecule 420 is pulled through the trench 180 by a longitudinal electrical field generated by the voltage source 417. When voltage is applied to electrodes 412 and 413 by the voltage source 417, the voltage generates the electric field (between reservoirs 414 and 415) that controllably (e.g., by turning on and off the voltage source 417) drives the DNA molecule 420 into and through the trench 180. Ammeter 418 monitors the ionic current change when DNA (or RNA) molecule 420 goes through trench 180. The ionic current (measured by the ammeter 418) flows through electrode 412, into the buffer solution 450, through the trench 180 (to interact with the target molecule 420 when present in the trench 180), out through the electrode 413.

A voltage source 419 is connected to top metal contact 114B and top metal contact 114A through the functionalized carbon nanotube 112, and the current is measured by ammeter 422. The ammeter 422 measures a change in current, which results from a change in conductance for the carbon nanotube 112. Note that conductance is inversely related to resistance. When no base of the DNA molecule 420 is attached (e.g., via the transient bond (such as a hydrogen bond)) to the carbon nanotube 112, the ammeter 422 measures a baseline current corresponding to no change in conductance (i.e., no change in resistivity) in the carbon nanotube 112. However, when the negatively charged DNA molecule 420 is in the trench 180 and when a DNA base attaches to (e.g., forms a transient bond to) the functionalized carbon nanotube 112, the conductance changes (i.e., increases) in the carbon nanotube 112 which causes the current measured by the ammeter 422 to change (i.e., increase). When respectively attached to the carbon nanotube 112, each negatively charged individual DNA (or RNA) base of the target molecule 420 causes the conductance to increase a predefined amount by providing detectable charge to the carbon nanotube 112. As a result of the increase in charge to the carbon nanotube 112, this increase in conductance causes a measured increase in current measured by the ammeter 422 to uniquely identify the attached DNA base. Each DNA base of the DNA molecule 420 causes a predefined change/increase in current that uniquely identifies the respective bases that consecutively pass underneath and attach to the carbon nanotube 112. Accordingly, the target molecule 420 is sequenced.

When the DNA base is attached to the carbon nanotube 112, the current flows into top metal contact 114B, into the carbon nanotube 112 (in which the attached DNA base interacts with the carbon nanotube 112 by providing charge resulting in an increase in the conductance of the carbon nanotube 112), out through the top metal contact 114A, into the ammeter 422 (to measure the current which has now changed (increase), and back to the voltage source 419. This base is identified according to the measured current, and the voltage source 417 is turned on to move (translocate) the DNA molecule 420 (i.e., break the transient bond), so that the next base can be measured and identified. This process continues until each base has been sequenced.

Now turning to an additional (simultaneous) technique for measuring the change in current to identify respective bases, another ammeter 421 monitors tunneling current between the carbon nanotube 112 and the bottom metal contact 106. In the system 400, a lead (shown with dashed lines) is also connected to the bottom metal contact 106 (e.g., underneath the nanodevice 100). A circuit is formed by the voltage source 419, the top metal contact 114B, the carbon nanotube 112 (the target molecule 420 when present), the buffer solution 450, and the ammeter 421. When the target molecule 420 is not present, the resistance is high because the buffer solution 450 does not contact (i.e., no electrical connection) carbon nanotube 112. Accordingly, the ammeter 421 measures a very small current (and/or no current) which is the baseline current for ammeter 421, when the target molecule 420 is not present and when no DNA base is attached to the carbon nanotube 112.

However, when the 417 drives the DNA molecule 420 into the trench underneath the carbon nanotube 112, the DNA base attaches to the carbon nanotube 112 above. This transient bond allows current (e.g., tunneling current) to flow, and the ammeter 421 measures the current that uniquely corresponds to (identifies) the type of base presently attached to carbon nanotube 112. For each different type of base that is respectively attached to the carbon nanotube 112, the ammeter 421 measures the current that identifies the particular DNA base (and/or RNA base). For example, when a particular DNA base of the DNA molecule 420 is attached (i.e., forms a transient bond to the carbon nanotube 112 above) to the carbon nanotube 112, current flows from the voltage source 419 into the top metal contact 114B, into the carbon nanotube 112, into the attached DNA/RNA base of the target molecule 420 (e.g., as tunneling current), into the buffer solution 450, out through the bottom metal electrode 106, into the ammeter 421 (for measuring and identifying the attached base), and back to the voltage source 419. The measured current is matched to a predefined current level (for a known base), and the attached based is identified as one of the known bases.

Note that the voltage sources 417 and 419, and the ammeters 418, 421, and 422 may be implemented in a computer system 700 (which may be computer test setup equipment) discussed further below.

Figure 5:
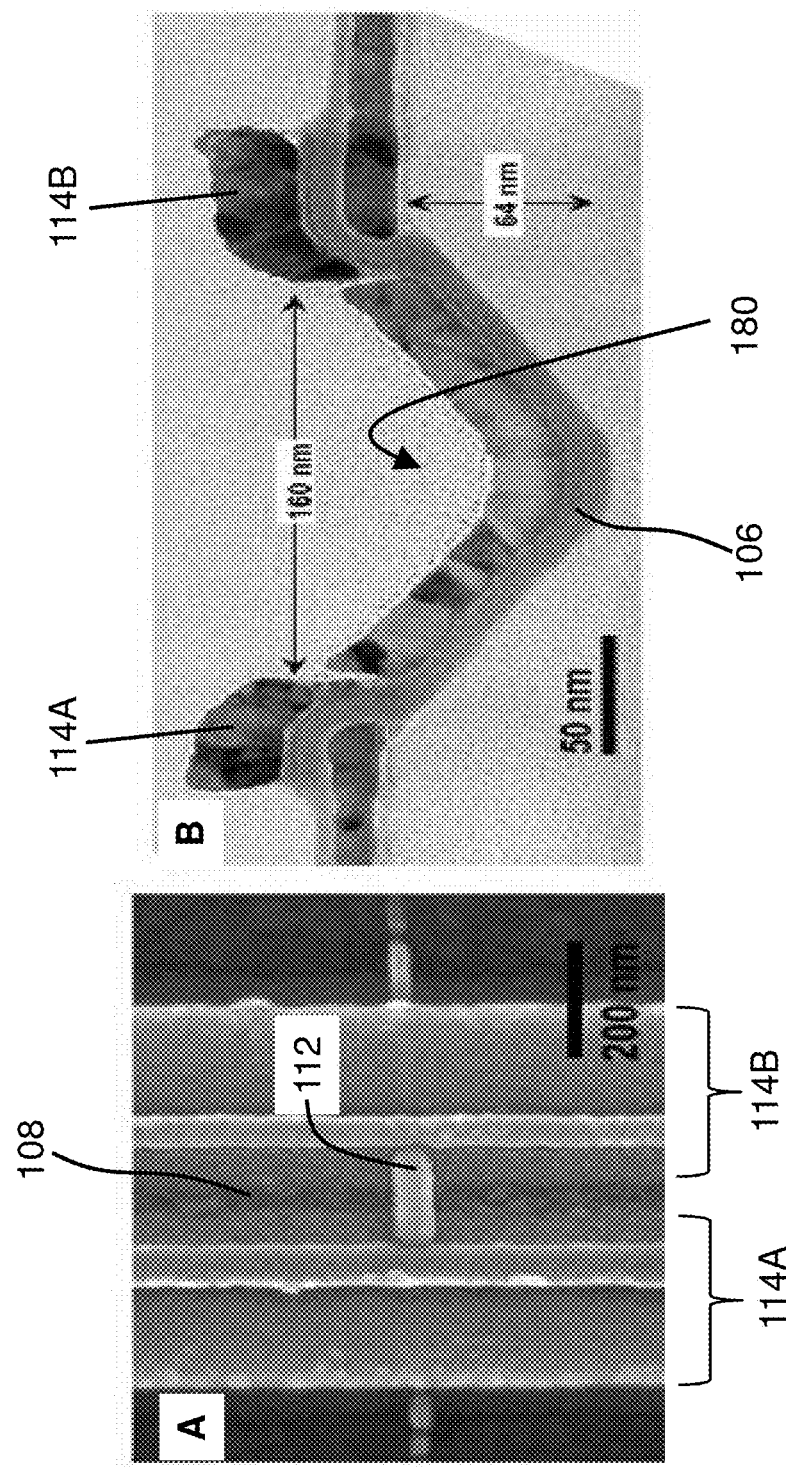
FIG. 5 illustrates a transmission electron microscope (TEM) of the device according to an embodiment.

FIG. 5 illustrates example view A and view B according to an embodiment. View A illustrates a top view of a scanning electron microscope image of the carbon nanotube 112 suspended over the trench 180 that was masked by top metal contacts 114 (Pd) on either side. Note that the carbon nanotube 112 has been coated with material so that the suspended carbon nanotube 112 is larger and can be more easily viewed in the electron microscope image. Also, the top metal contacts 114 include additional metal patterned on top.

View B illustrates a cross-sectional view of a transmission electron microscope image of a large trench 180 formed in device 100 that was masked by top metal contacts 114 on either side of the trench 180. The carbon nanotube 112 is not visible. Also, this example does not show the <110> crystal orientation for the nonconducting material 110 but shows a different crystal orientation for the nonconducting material 110. As such, the trench 180 has a v shape because of isotropic etching that occurred. Note that the trench 180 has additional metal on top of the embedded bottom metal contact 106.

FIG. 6 illustrates a method of forming device 100 for sequencing according to an embodiment. Reference can be made to FIGS. 1-5 discussed above, along with FIGS. 7 and 8 below.

The bottom metal contact 106 is disposed/embedded at the location 108 in an insulator (e.g., the oxide layer 104) that is on the substrate 102 at block 605.

The nonconducting material 110 is disposed on top of the embedded bottom metal contact 106 and the insulator (oxide layer 104) at block 610.

The carbon nanotube 112 is disposed on top of the nonconducting material 110 at block 615.

At block 620, the top metal contacts 114 are disposed and patterned on top of the carbon nanotube 112 at the location 108 of the bottom metal contact 106, where the top metal contacts 114A and 114B are formed at opposing ends of the carbon nanotube 112 at the location 108 (as shown in FIG. 1C).

At block 625, the carbon nanotube 112 is suspended over the bottom metal contact 106 at the location 108, by etching away the nonconducting material 110 under the carbon nanotube 112 to expose the embedded bottom metal contact 106 as a bottom of a trench 180, while leaving the nonconducting material immediately under the metal contacts as walls of the trench (as shown in FIGS. 1D, 2, and 3).

The carbon nanotube 112 is suspended over the trench 180 without touching the bottom metal contact 106. The top metal contacts 114A and 114B are on opposing sides of the trench 180. The top metal contacts 114A and 114B are electrically connected to one another through the carbon nanotube 112.

As illustrated in FIG. 4, the trench 180 is filled with buffer solution 450 such that the buffer solution 450 does not contact the top metal contacts 114 and does not contact the carbon nanotube 112. In another case, the trench 180 is filled with the buffer solution 450 fully such that the buffer solution 450 does contact (both) the top metal contacts 114 and the carbon nanotube 112.

A thickness of the nonconducting material 110 determines a depth of the trench 180. A distance separating the top metal contacts 114A and 114B determines a width of the trench 180. A length of the top metal contacts 114A and 114B determines the length of the trench 180 (e.g., from front to back).

Additionally, the device 100 can have multiple trenches 180 each having its own corresponding bottom metal contact 106, where one carbon nanotube 112 is respectively suspended over one of the multiple trenches 180 on a one-to-one basis in order for each carbon nanotube 112 to be individually used to measure the current (as discussed herein) in each respective trench 180.

FIG. 7 illustrates a method of operating the nanodevice 100 for sequencing the target molecule 420 (such as, e.g., a DNA molecule, RNA molecule, protein, and/or any type of biomolecule having nucleotides (or bases) as understood by one skilled in the art) according to an embodiment. Reference can be made to FIGS. 1-6 discussed above, along with FIG. 8 below.

At block 705, voltage (including an electric field) of the voltage source 417 (e.g., which may be implemented in the computer system 700) translocates the (negatively charged) target molecule 420 through the trench 180 (on the substrate 102) of the nanodevice 100 in which the nanodevice 100 includes the carbon nanotube 112 suspended over the trench 180 by top metal contacts 114, and includes the bottom metal contact 106 as the bottom of the trench 180.

The buffer solution 450 passes both below and above the carbon nanotube 112, where the carbon nanotube 112 is functionalized with an organic compound having two different functional groups on either end (of the organic compound) in which one functional group attaches to the carbon nanotube 112 and the other functional group interacts with the target molecule 420 (e.g., DNA strand).

A first current flowing between the top metal contacts through the carbon nanotube is measured at block 710. A change in the first current is measured based on a base of the target molecule 420 in the trench interacting with the carbon nanotube 112 to change a conductance of the carbon nanotube 112 at block 715. For example, the ammeter 422 (e.g., which may be implemented in the computer system 700) is configured to measure (first) current flowing between the top metal contacts 114A and 114B through the carbon nanotube 112. The ammeter 422 is configured measure a change in the (first) current based on a base (e.g., DNA/RNA base) of the target molecule 420 in the trench 180 interacting (and attached) with the carbon nanotube 112 to change a conductance (G) of carbon nanotube 112. The type of base of the target molecule 420 is identified according to the change in current measured (e.g., matched to a known base).

Also, the ammeter 421 (e.g., which may be implemented in the computer system 800) is configured to measure current flowing between the carbon nanotube 112 and the embedded bottom metal contact 106, which may be zero or close to zero when no base is attached to the carbon nanotube 112. The ammeter 421 (e.g., which may be implemented in the computer system 800) is configured to measure a change in the current based a base of the target molecule 420 in the trench interacting (and attached) with the carbon nanotube 112 to provide an electrical current path (e.g., for tunneling current) between the carbon nanotube 112 and the bottom metal contact 106. As such, the base of the target molecule 420 is identified according to the change in current measured.

Using the computer 800, each base may be simultaneously measured by the first current (via ammeter 422) and the second current (via ammeter 421) to identify the base presently attached to the suspended carbon nanotube 112. Although each of the first current and the second current are capable of identifying the type of base, measuring both bases (simultaneously) provides double verification of for the type of base. The computer 800 can store the time when both the first and second currents are measured for the (same) particular base so that the identified base can be cross checked. Note that voltage of the voltage source 417 may be pulsed to move the target molecule 420 one base at a time through the trench 180 until all of the bases have been sequenced.

Figure 8:
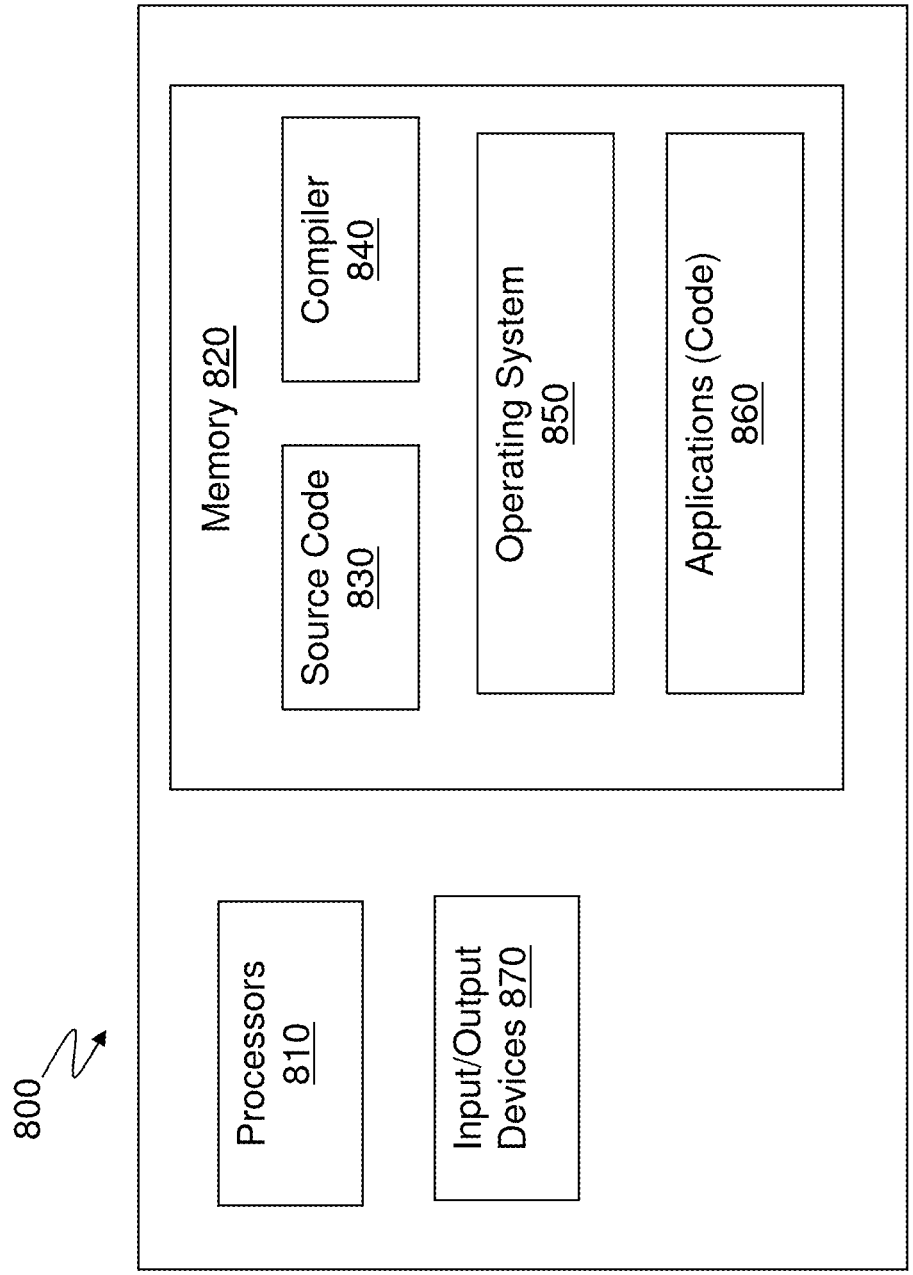
FIG. 8 is a block diagram that illustrates an example of a computer (computer test setup) having capabilities, which may be included in and/or combined with embodiments.

FIG. 8 illustrates an example of a computer 800 (e.g., as part of the computer test setup for testing and analysis) which may implement, control, and/or regulate the respective voltages of the voltage sources, respective measurements of the ammeters, and display screens for displaying various current amplitude (including ionic current and transistor (source to drain current)) as discussed herein. The computer 800 also stores the respective electrical current amplitudes of each base tested and measured to be compared against the baselines current amplitudes of different bases, which is utilized to identify the bases of the tested/target molecule.

Various methods, procedures, modules, flow diagrams, tools, applications, circuits, elements, and techniques discussed herein may also incorporate and/or utilize the capabilities of the computer 800. Moreover, capabilities of the computer 800 may be utilized to implement features of exemplary embodiments discussed herein. One or more of the capabilities of the computer 800 may be utilized to implement, to connect to, and/or to support any element discussed herein (as understood by one skilled in the art) in FIGS. 1-7. For example, the computer 800 which may be any type of computing device and/or test equipment (including ammeters, voltage sources, current meters, connectors, etc.). Input/output device 870 (having proper software and hardware) of computer 800 may include and/or be coupled to the nanodevices and structures discussed herein via cables, plugs, wires, electrodes, patch clamps, etc. Also, the communication interface of the input/output devices 870 comprises hardware and software for communicating with, operatively connecting to, reading, and/or controlling voltage sources, ammeters, and current traces (e.g., magnitude and time duration of current), etc., as discussed and understood herein. The user interfaces of the input/output device 870 may include, e.g., a track ball, mouse, pointing device, keyboard, touch screen, etc., for interacting with the computer 800, such as inputting information, making selections, independently controlling different voltages sources, and/or displaying, viewing and recording current traces for each base, molecule, biomolecules, etc.

Generally, in terms of hardware architecture, the computer 800 may include one or more processors 810, computer readable storage memory 820, and one or more input and/or output (I/O) devices 870 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 810 is a hardware device for executing software that can be stored in the memory 820. The processor 810 can be virtually any custom made or commercially available processor, a central processing unit (CPU), a data signal processor (DSP), or an auxiliary processor among several processors associated with the computer 800, and the processor 810 may be a semiconductor based microprocessor (in the form of a microchip) or a macroprocessor.

The computer readable memory 820 can include any one or combination of volatile memory elements (e.g., random access memory (RAM), such as dynamic random access memory (DRAM), static random access memory (SRAM), etc.) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 820 may incorporate electronic, magnetic, optical, and/or other types of storage media. Note that the memory 820 can have a distributed architecture, where various components are situated remote from one another, but can be accessed by the processor 810.

The software in the computer readable memory 820 may include one or more separate programs, each of which comprises an ordered listing of executable instructions for implementing logical functions. The software in the memory 820 includes a suitable operating system (O/S) 850, compiler 840, source code 830, and one or more applications 860 of the exemplary embodiments. As illustrated, the application 860 comprises numerous functional components for implementing the features, processes, methods, functions, and operations of the exemplary embodiments.

The operating system 850 may control the execution of other computer programs, and provides scheduling, input-output control, file and data management, memory management, and communication control and related services.

The application 860 may be a source program, executable program (object code), script, or any other entity comprising a set of instructions to be performed. When a source program, then the program is usually translated via a compiler (such as the compiler 840), assembler, interpreter, or the like, which may or may not be included within the memory 820, so as to operate properly in connection with the O/S 850. Furthermore, the application 860 can be written as (a) an object oriented programming language, which has classes of data and methods, or (b) a procedure programming language, which has routines, subroutines, and/or functions.

The I/O devices 870 may include input devices (or peripherals) such as, for example but not limited to, a mouse, keyboard, scanner, microphone, camera, etc. Furthermore, the I/O devices 870 may also include output devices (or peripherals), for example but not limited to, a printer, display, etc. Finally, the I/O devices 870 may further include devices that communicate both inputs and outputs, for instance but not limited to, a NIC or modulator/demodulator (for accessing remote devices, other files, devices, systems, or a network), a radio frequency (RF) or other transceiver, a telephonic interface, a bridge, a router, etc. The I/O devices 870 also include components for communicating over various networks, such as the Internet or an intranet. The I/O devices 870 may be connected to and/or communicate with the processor 810 utilizing Bluetooth connections and cables (via, e.g., Universal Serial Bus (USB) ports, serial ports, parallel ports, FireWire, HDMI (High-Definition Multimedia Interface), etc.).

In exemplary embodiments, where the application 860 is implemented in hardware, the application 860 can be implemented with any one or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

What is claimed is:

1. A method of forming a nanodevice for sequencing, the method comprising:
    disposing a bottom metal contact at a location in an insulator that is on a substrate;
    disposing a nonconducting material on top of the bottom metal contact and the insulator;
    disposing a carbon nanotube on top of the nonconducting material;
    disposing top metal contacts on top of the carbon nanotube at the location of the bottom metal contact, wherein the top metal contacts are formed at opposing ends of the carbon nanotube at the location; and
    suspending the carbon nanotube over the bottom metal contact at the location, by etching away the nonconducting material under the carbon nanotube to expose the bottom metal contact as a bottom of a trench, while leaving the nonconducting material immediately under the top metal contacts as walls of the trench.

2. The method of claim 1, wherein the carbon nanotube is suspended over the trench.

3. The method of claim 1, wherein the top metal contacts are on opposing sides of the trench.

4. The method of claim 1, wherein the top metal contacts are electrically connected to one another through the carbon nanotube.

5. The method of claim 1, further comprising filling the trench with buffer solution such that the buffer solution does not contact the top metal contacts and the carbon nanotube.

6. The method of claim 1, further comprising filling the trench with buffer solution fully such that the buffer solution does contact the top metal contacts and the carbon nanotube.

7. The method of claim 1, wherein a thickness of the nonconducting material determines a depth of the trench.

8. The method of claim 1, wherein a distance separating the top metal contacts determines a width of the trench.

9. The method of claim 1, wherein a length of the top metal contacts determines a length of the trench.

10. A method of sequencing, the method comprising:
    translocating a target molecule in a trench on a substrate of a nanodevice, wherein the nanodevice includes a carbon nanotube suspended over the trench by top metal contacts, and includes a bottom metal contact as a bottom of the trench;
    passing a buffer solution both below and above the carbon nanotube, wherein the carbon nanotube is functionalized with an organic compound having two different functional groups on either end in which one functional group attaches to the carbon nanotube and another functional group interacts with the target molecule;
    measuring a first current flowing between the top metal contacts through the carbon nanotube; and
    measuring a change in the first current based on a base of the target molecule in the trench interacting with the carbon nanotube to change a conductance of the carbon nanotube.

11. The method of claim 10, wherein the base of the target molecule is identified according to the change in first current measured.

12. The method of claim 10, further comprising measuring a second current flowing between the carbon nanotube and the bottom metal contact; and measuring a change in the second current based the base of the target molecule in the trench interacting with the carbon nanotube to provide an electrical current path between the carbon nanotube and the bottom metal contact.

13. The method of claim 12, wherein the base of the target molecule is identified according to the change in second current measured.

* * * * *